(12) United States Patent  
Tockman et al.

(10) Patent No.: US 7,515,969 B2  
(45) Date of Patent: Apr. 7, 2009

(54) SENSOR GUIDED EPICARDIAL LEAD

(75) Inventors: Bruce A. Tockman, Scandia, MN (US); Randy Westlund, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 559 days.

(21) Appl. No.: 10/930,088

(22) Filed: Aug. 31, 2004

(65) Prior Publication Data

US 2006/0047333 A1  Mar. 2, 2006

(51) Int. Cl.  
    *A61N 1/05*  (2006.01)
(52) U.S. Cl. ..................................... 607/122
(58) Field of Classification Search .......... 607/115, 607/122  
    See application file for complete search history.

(56) References Cited

U.S. PATENT DOCUMENTS

| | | | | |
|---|---|---|---|---|
| 4,046,151 | A | * | 9/1977 | Rose ........................ 607/127 |
| 4,701,185 | A | | 10/1987 | Eckstein |
| 5,070,882 | A | * | 12/1991 | Bui et al. ................... 600/466 |
| 5,275,166 | A | | 1/1994 | Vaitekunas et al. |
| 5,366,496 | A | | 11/1994 | Dahl et al. |
| 5,740,808 | A | * | 4/1998 | Panescu et al. ............. 600/424 |
| 5,938,602 | A | * | 8/1999 | Lloyd ........................ 600/424 |
| 5,954,649 | A | * | 9/1999 | Chia et al. .................. 600/424 |
| 5,968,085 | A | * | 10/1999 | Morris et al. ............... 607/116 |
| 6,363,278 | B1 | | 3/2002 | Stahmann et al. |
| 6,411,848 | B2 | | 6/2002 | Kramer et al. |
| 6,501,988 | B2 | | 12/2002 | Kramer et al. |
| 6,512,952 | B2 | | 1/2003 | Stahmann et al. |
| 6,574,506 | B2 | | 6/2003 | Kramer et al. |
| 6,574,514 | B2 | | 6/2003 | Patridge et al. |
| 6,597,951 | B2 | | 7/2003 | Kramer et al. |
| 6,738,674 | B2 | * | 5/2004 | Osypka ...................... 607/122 |
| 6,970,733 | B2 | * | 11/2005 | Willis et al. ................. 600/424 |
| 7,004,173 | B2 | * | 2/2006 | Sparks et al. ............... 128/898 |
| 7,267,650 | B2 | * | 9/2007 | Chow et al. ................. 600/467 |

\* cited by examiner

*Primary Examiner*—Carl H Layno  
*Assistant Examiner*—Brian T Gedeon  
(74) *Attorney, Agent, or Firm*—Hollingsworth & Funk, LLC

(57) ABSTRACT

Implantable cardiac monitoring and stimulation methods and devices with epicardial leads having sensor feedback. A fixed or extendable/retractable sensor may be displaceable within the lead's lumen and configured to sense the presence of an anatomical feature or physiological parameter of cardiac tissue in proximity with the lead body's distal end. The sensor may include an ultrasonic sensing element, a perfusion sensor, a photoplethysmographic sensor, or a blood oximetry sensor. Methods of determining suitability for implanting a lead involve the steps of accessing an epicardial surface of the heart, and moving the cardiac lead to an implant site at the epicardial surface. A transmitted signal is directed at the implant site. A reflected signal is received, indicative of the presence of a blood vessel at the implant site. A determination may be made to determine whether the implant site is suitable or unsuitable based on the reflected signal.

8 Claims, 9 Drawing Sheets

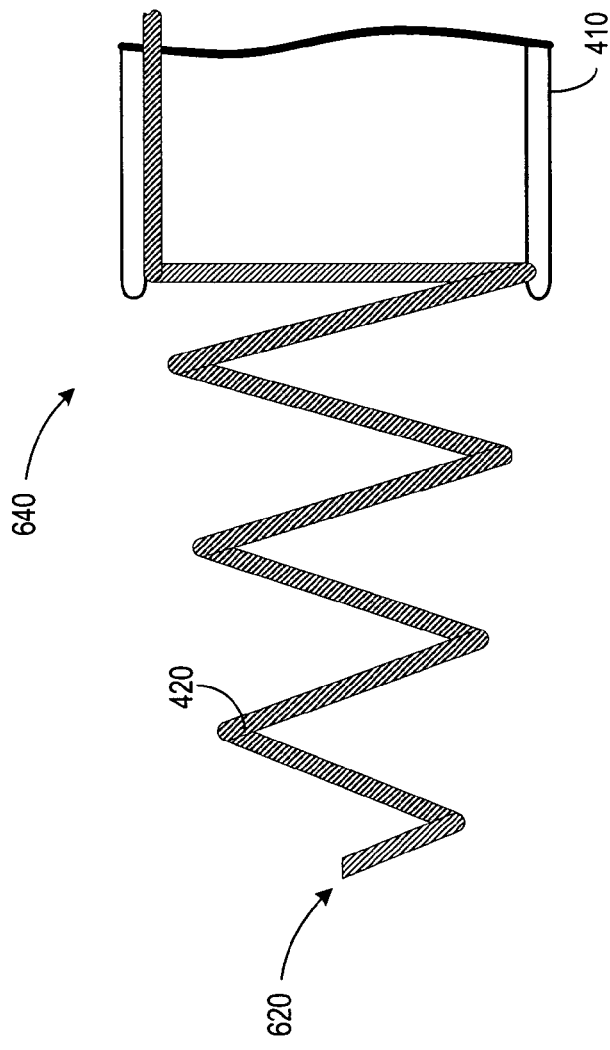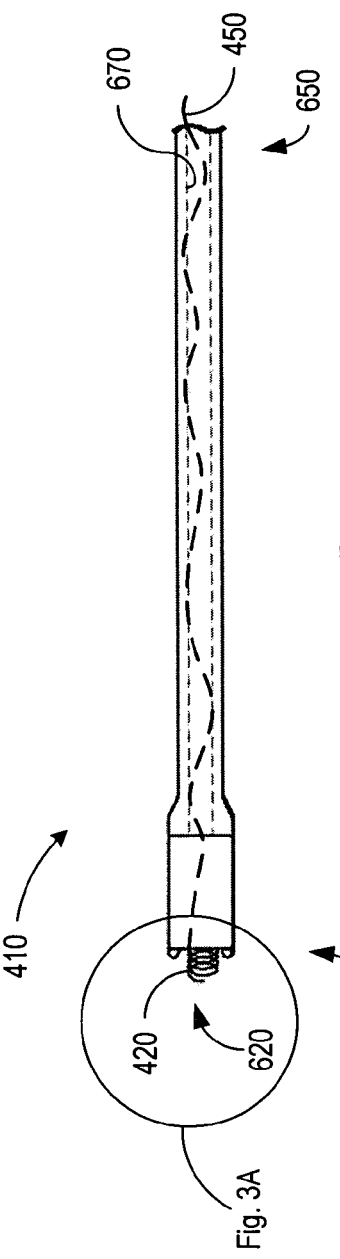

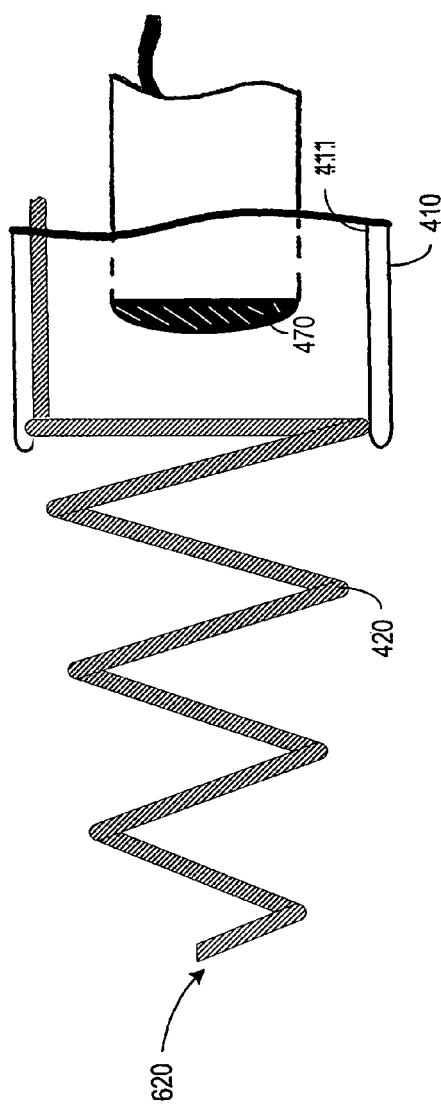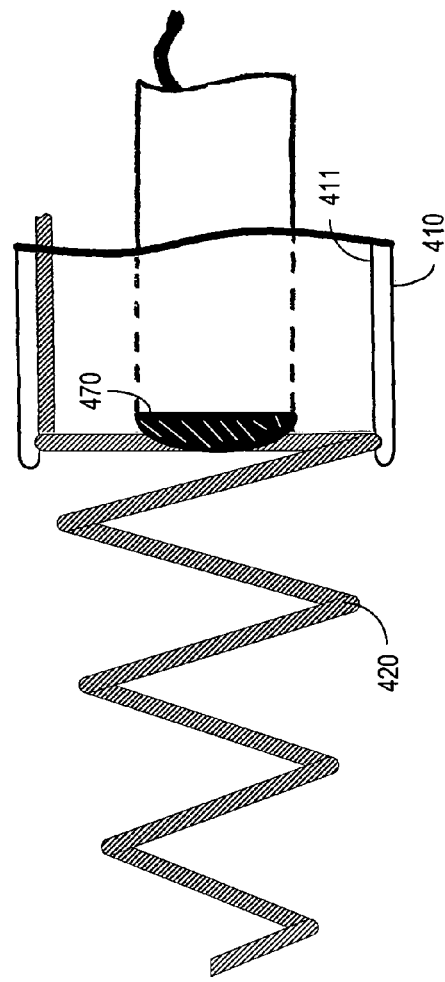
Fig. 4A
Fig. 4B

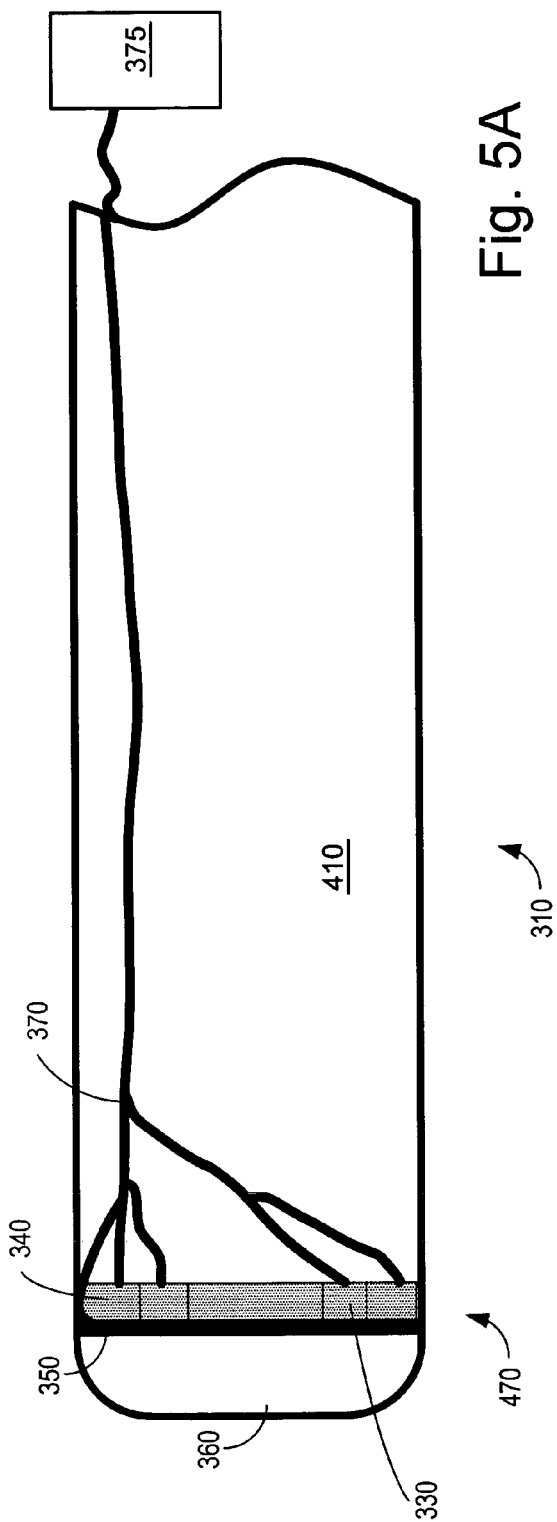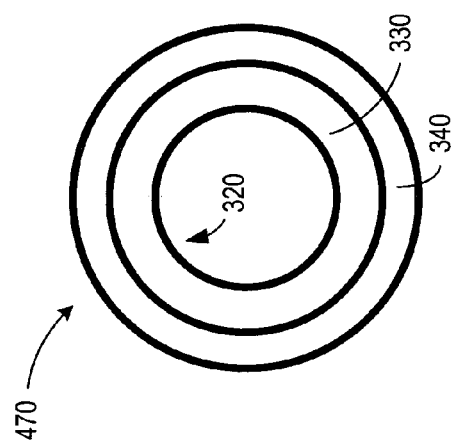

SENSOR GUIDED EPICARDIAL LEAD

FIELD OF THE INVENTION

The present invention relates generally to leads for implantable cardiac monitoring and stimulation devices and, more particularly, to epicardial leads having sensor feedback capabilities.

BACKGROUND OF THE INVENTION

Rhythmic contractions of a healthy heart are normally initiated by the sinoatrial node that includes specialized cells located in the superior right atrium. The sinoatrial node is the normal pacemaker of the heart, typically initiating 60-100 heartbeats per minute. When the sinoatrial node is pacing the heart normally, the heart is said to be in normal sinus rhythm (NSR).

The heart has specialized conduction pathways in both the atria and the ventricles that enable the rapid conduction of excitation impulses (i.e. depolarizations) from the sinoatrial node throughout the myocardium. These specialized conduction pathways conduct the depolarizations from the sinoatrial node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways may suffer compromised cardiac output, such as that associated with congestive heart failure.

Cardiac rhythm management devices have been developed that provide pacing stimulation to one or more heart chambers in an attempt to improve the rhythm and coordination of atrial and/or ventricular contractions. Cardiac rhythm management devices may incorporate defibrillation and/or pacemaker circuitry used to treat patients with serious arrhythmias. Cardiac rhythm management devices typically include circuitry to sense signals from the heart and a pulse generator for providing electrical stimulation to the heart. One or more leads are typically delivered transvenously or transthoracically into the heart, and are coupled to electrodes that contact the myocardium for sensing the heart's electrical signals and for delivering stimulation to the heart in accordance with various therapies. Cardiac rhythm management devices may deliver low energy electrical pace pulses timed to assist the heart in producing a contractile rhythm that maintains cardiac pumping efficiency appropriate to meet the metabolic requirements of the patient.

While transvenous lead delivery is appropriate for many patients that experience adverse synchronization conditions, there are a significant number of patients who could benefit from cardiac resynchronization therapy or other cardiac stimulation therapies, but are not good candidates for transvenous lead implantations. Many of these patients are considered poor candidates for transvenous lead implantation for various reasons, including inability to locate the coronary sinus, presence of coronary sinus stenosis, inability to catheterize a desired branch vein, instability of the transvenous lead, or an unacceptably high pacing threshold, for example.

For procedures utilizing epicardial lead placement, many challenges sometimes make lead placement difficult or impossible. If the target implantation site is on the posterior or lateral wall of the left ventricle, it may be difficult to deploy an endoscope to allow visualization of the myocardial surface. Without visualization, lead placement may be difficult or impossible. This is especially true if the entry point is subxiphoid. Without visualization, there is a risk that the lead may be inserted into fat or a coronary artery or blood vessel.

SUMMARY OF THE INVENTION

The present invention is directed to implantable cardiac monitoring and stimulation devices and methods using cardiac leads having sensor feedback during the implantation procedure. A sensor, such as a blood-flow or perfusion sensor, for example, detects the presence of coronary vessels in front of the lead prior to implantation. The sensor provides feedback to the clinician to assist in lead placement.

Embodiments of a cardiac lead in accordance with the present invention include a lead body having a proximal end, a distal end, and a lumen defined between the proximal and distal ends. One or more electrical conductors extend from the proximal end to at least the distal end of the lead. At least one electrode is configured for epicardial implantation and situated near the distal end of the lead body and coupled to at least one electrical conductor.

Embodiments include a sensor that is displaceable within the lumen of the lead body and configured to sense the presence of an anatomical feature or a physiological parameter of cardiac tissue in proximity with the lead body's distal end. The electrode of the cardiac lead may be extendable distally from the distal end of the lead body and/or may extend out the side of the lead body. In alternate embodiments, the sensor may sense blood presence or flow in tissue, and may be extendable at least between the distal end of the lead body and a distal end of the electrode. The electrode may be configured as an active fixation arrangement engagable with the epicardium or myocardium, and may be configured as a helical fixation arrangement and/or an extendable/retractable helical fixation arrangement. The electrode may also be configured to at least partially encircle the sensor.

The sensor may include an ultrasonic sensing element, such as a piezoelectric element adapted to provide ultrasonic Doppler blood-flow sensing, a perfusion sensor, a photoplethysmographic sensor, a blood oximetry sensor, or other sensor configured to sense the presence of an anatomical feature or a physiological parameter of cardiac tissue in proximity with the lead body's distal end. The perfusion sensor may be configured to differentiate between myocardial tissue including blood vessels and myocardial tissue without blood vessels using a colormetric measurement.

In embodiments of a cardiac lead system in accordance with the present invention, a lead has a proximal end and a distal end, and includes one or more electrical conductors. An electrode is configured for epicardial implantation and coupled to at least one of the electrical conductors. A sensor is provided with the lead. Control circuitry is coupled to the sensor and to the electrode, the control circuitry adapted to detect the presence of an anatomical feature or a physiological parameter of cardiac tissue. The control circuitry may be adapted to perform a pacing threshold test, and may be integral to a device programmer and/or a pulse generator.

The sensor may sense blood presence or flow in tissue using, for example, an ultrasound sensor such as an ultrasonic Doppler blood-flow sensor, a perfusion sensor, a sensor adapted to perform photoplethysmography, a sensor that detects blood oximetry, or a tissue impedance sensor. The sensor may be displaceable within a lumen of the lead.

The electrode may include an extendable/retractable fixation element and may be configured to form a helix that at least partially encircles the sensor. The system may include a fixation element adjacent the sensor. A lead introducer may be provided with the system, having a lead channel configured to receive the lead. The lead introducer may be configured to guide the lead to an epicardial surface of a patient's heart.

Embodiments of the present invention are directed to methods of determining suitability for implanting a cardiac lead on a surface of a patient's heart. Various embodiments identify suitable pacing sites, even in the presence of epicardial fat and tissue adhesions. Methods may involve the steps of accessing, via a patient's chest cavity, an epicardial surface of the heart, moving the cardiac lead to an implant site at the epicardial surface, and stabilizing the lead at the implant site. A transmitted signal may be directed at the implant site. A reflected signal resulting from the transmitted signal may be received that is indicative of the presence of a blood vessel at the implant site. The presence of an anatomical feature or a physiological parameter of cardiac tissue at the implant site may then be determined using the reflected signal. The implant site is determined to be suitable or unsuitable for implantation of the cardiac lead based at least in part on the presence or absence of the anatomical feature or the physiological parameter.

The physiological parameter may be a pacing threshold, an R-wave, or tissue impedance, for example. The parameter may be used to determine implantation site suitability, such as by determining presence or absence of blood vessels at the implant site using the reflected signal, confirming an absence of blood vessels at the implant site using the reflected signal, and confirming an acceptable pacing threshold at the implant site. Blood-flow signals representative of blood vessels near or at the implant site may be generated using the reflected signal. The transmitted signal and reflected signal may be effected in accordance with a photoplethysmographic technique or a pulse oximetric technique, for example.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 3A illustrates a magnified view of the distal portion, identified in FIG. 3B, of an embodiment of a lead having an ultrasonic Doppler flow sensor arrangement in accordance with the present invention;

FIG. 3B illustrates a lead in accordance with the present invention, identifying the magnified portion illustrated in FIG. 3A;

FIG. 4A illustrates a sensor guided epicardial lead in accordance with the present invention, with the sensor placed proximal to the distal end of a lead;

FIG. 4B illustrates a sensor guided epicardial lead in accordance with the present invention, with the sensor placed even with the end of a lead;

FIG. 5A is a magnified plan view of the distal end of a lead incorporating a Doppler blood-flow sensor in accordance with embodiments of the present invention;

FIG. 5B is a magnified end view of the lead illustrated in FIG. 5A, illustrating annular array elements of the Doppler sensor;

Figure 1:
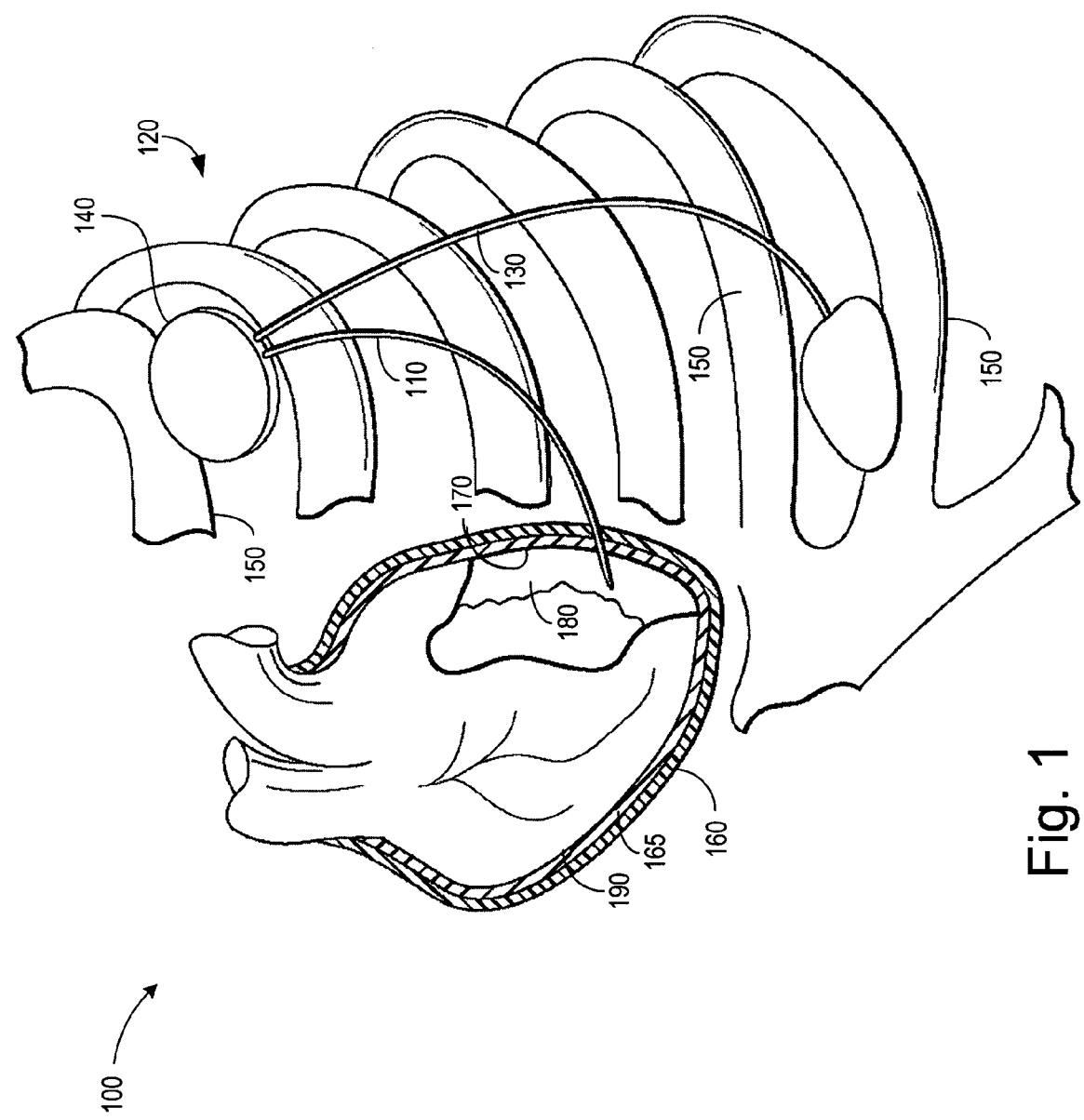
FIG. 1 illustrates a cardiac monitoring and/or stimulation device in accordance with the present invention, as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

Methods and devices employing an implantable cardiac lead in accordance with the present invention may incorporate one or more of the features, structures, methods, or combinations thereof described herein below. For example, devices and/or leads having sensing arrangements to provide feedback to the clinician during implantation may be implemented to include one or more of the features and/or processes described below. It is intended that such a device or method need not include all of the features and functions described herein, but may be implemented to include selected features and functions that, alone or in combination, provide for useful structures and/or functionality.

Leads and systems in accordance with the present invention that incorporate sensing arrangements to provide feedback to the clinician during implantation may be used to facilitate epicardial surface lead placement, epicardial fixed lead placement, endocardial lead placement, or intramyocardial lead placement, for example. FIG. 1 illustrates a cardiac monitoring and/or stimulation system 100 in accordance with an embodiment of the present invention, as implanted in a patient. In general terms, a lead 110 implemented in accordance with the present invention may be used with a cardiac monitoring and/or stimulation device. One such device is an implantable cardiac monitoring and/or stimulation (ICMS) device 120 that includes a housing or can 140 implanted under the skin in the abdominal or chest region of a patient.

The can 140 of the ICMS device 120 may be configured for positioning outside of the rib cage at an intercostal or subcostal location, within the abdomen, or in the upper chest region and include one or more epicardial leads 110 having one or more electrodes implanted within myocardial tissue of the heart. Although a single lead 110 is shown implanted in the left ventricular wall in FIG. 1, it is understood that one or more other leads 110 may be implanted in myocardial tissue or on the epicardial surface of one or more heart chambers other than, or in addition to, the left ventricle, or that other leads, such as endocardial leads or subcutaneous leads 130, may be used in combination with one or more epicardial leads 110.

The lead 110 shown in FIG. 1 is connected to the can 140 of the ICMS device 120. The can 140 (electrically active or inactive) is positioned external of the patient's rib cage 150. The lead 110 extends from the can 140, through the intercostal space (or under the xiphoid process, for example), and into the thoracic cavity. The lead 110 penetrates the pericardium 160 and may extend into or through a pericardial cavity 165. An electrode of the lead 110 penetrates the epicardium 170 and is implanted in the myocardium 180 of the heart 190.

The ICMS device 120 may also be used with other leads, such as a subcutaneous lead 130. The subcutaneous lead 130 may be used for monitoring and/or stimulation in combination with one or more of the lead(s) 110. For example, subcutaneous leads that may be used in cooperation with the ICMS system 100 are disclosed in commonly owned U.S. patent application Ser. No. 10/465,520, filed Jun. 19, 2003 now U.S. Publication No. 2004/0230230, which is hereby incorporated herein by reference. One or more leads 110 may further be used in combination with a subcutaneous monitoring and/or stimulation device of the type disclosed in commonly owned U.S. patent application Ser. No. 10/820,642 and Ser. No. 10/821,248 now Publication Nos. 2004/0215258 and 2004/0215240, filed concurrently on Apr. 8, 2004, which are hereby incorporated herein by reference.

The ICMS device 120 shown in FIG. 1 is intended to be representative of various types of cardiac rhythm management devices. Such devices include, for example, implantable pulse generators such as pacemakers and implantable cardioverter/defibrillators that provide electrical stimulation to selected chambers of the heart. A pacemaker, for example, is an implantable pulse generator that paces the heart with timed pacing pulses. Control circuitry in the pacemaker may be adapted to perform pacing threshold tests, tissue impedance tests, and other tests for determining useful physiologic and device parameters. ICMS devices also typically employ processors useful for signal processing and other algorithmic operations, as is well understood in the art.

Pacemakers are particularly useful in treating bradycardia, where the ventricular rate is too slow. Atrio-ventricular conduction defects (i.e., AV block) that are permanent or intermittent and sick sinus syndrome represent common causes of bradycardia for which permanent pacing may be indicated. If functioning properly, the pacemaker serves to correct the heart's inability to pace itself at an appropriate rhythm in order to meet metabolic demand by enforcing a minimum heart rate.

Another embodiment of the ICMS device 120 is a cardiac resynchronization device, which monitors and regulates the degree to which the heart chambers contract in a coordinated manner during a cardiac cycle to effect efficient pumping of blood. The heart has specialized conduction pathways in both the atria and the ventricles that enable the rapid conduction of muscle excitation throughout the myocardium. These pathways conduct excitatory impulses from the sino-atrial node to the atrial myocardium, to the atrio-ventricular node, and then to the ventricular myocardium to facilitate coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency may be greatly diminished. Patients who exhibit pathology of these conduction pathways, such as bundle branch blocks, can thus suffer from compromised cardiac output.

Heart failure, for example, is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF may be due to a variety of etiologies, with ischemic heart disease being the most common. Some CHF patients suffer from some degree of AV block or are chronotropically deficient such that their cardiac output may be improved with conventional bradycardia pacing. Such pacing, however, may result in some degree of uncoordination in atrial and/or ventricular contractions due to the way in which pacing excitation is spread throughout the myocardium. The resulting diminishment in cardiac output may be significant in a CHF patient whose cardiac output is already compromised. Intraventricular and/or interventricular conduction defects (e.g., bundle branch blocks) are also commonly found in CHF patients.

The ICMS device 120 may be configured to treat these problems, such as by providing electrical pacing stimulation to one or both ventricles in an attempt to improve the coordination of ventricular contractions, termed cardiac resynchronization therapy. The ICMS device 120 may be configured structurally and functionally in a manner described in commonly owned U.S. Pat. Nos. 6,597,951; 6,574,506; 6,512, 952; 6,501,988; 6,411,848; and 6,363,278, each of which is hereby incorporated herein by reference.

Figure 2:
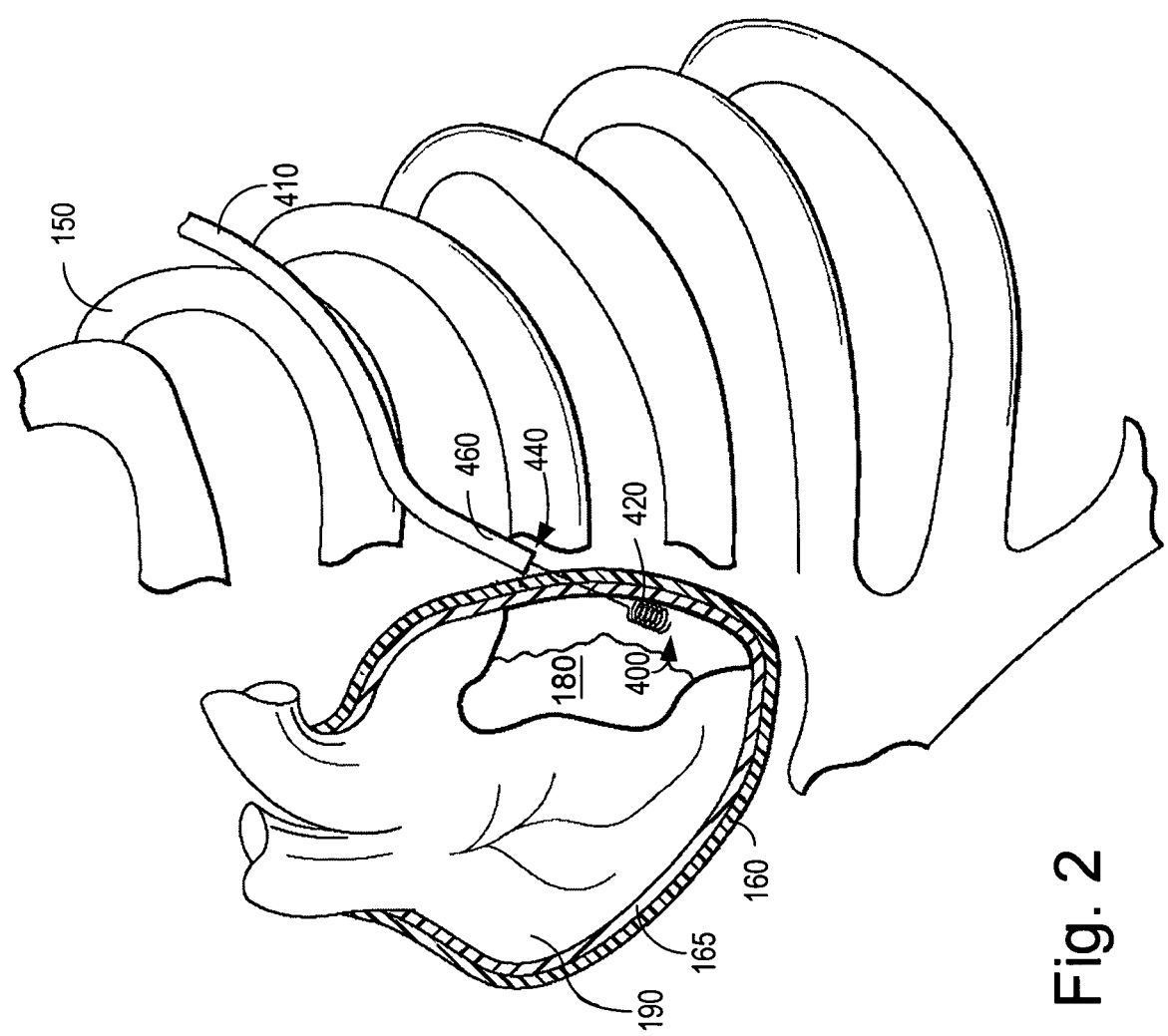
FIG. 2 illustrates a lead having a helical fixation arrangement in the myocardium placed in accordance with an embodiment of the present invention.

Turning now to FIG. 2, there is illustrated a lead 410 having a helical electrode 420 implanted in the myocardium 180 in accordance with an embodiment of the present invention. After locating a suitable implantation site, as will be described more fully below, the electrode 420 is implanted within the myocardium 180 typically by rotating the lead 410. In another embodiment, the electrode 420 may be inserted into the myocardium 180 and actively extended out from the lead and into myocardial tissue, such as distally out from the end of the lead, out from the side of the lead, or out from another location of the lead.

As the lead 410 is rotated, the sharp end 400 of the helical electrode 420 engages myocardial tissue and penetrates into the myocardium 180. As the lead 410 is further rotated, the sharp end 400 burrows through the tissue, penetrating further into myocardial tissue and acutely fixing the electrode within the myocardium 180. This process effectively screws the helical electrode 420 into the myocardial tissue.

Although the helical electrode 420 is illustrated having uniform pitch, cylindrical cross-section, and constant coil thickness, it is contemplated that any helical or screw-like structure, as well as other fixation elements such as, tines, barbs, and mechanical fasteners, may be used in accordance with the present invention. In the example of the helical electrode 420, the helix may be of non-uniform and/or tapering cross-section, the pitch may be non-uniform, and the shape and thickness of the coil may be varied, for example. Electrodes and fixation arrangements in accordance with the present invention may be combined with leads such as, for example, those disclosed in commonly assigned U.S. Pat. No. 5,496,362, which is hereby incorporated herein by reference. Additional details of fixation approaches involving surface texturing, selective material use, and other arrangements that facilitate lead fixation via tissue ingrowth are disclosed in commonly owned U.S. patent application Ser. No. 10/004, 708 filed Dec. 4, 2001 now U.S. Pat. No. 6,961,621, which is hereby incorporated herein by reference.

Referring now to FIGS. 3A and 3B, the lead 410 includes an electrical conductor 450 (FIG. 3B) that is electrically insulated from surrounding tissue through its length and terminates in the distal, pace/sense, helical electrode 420. The helical electrode 420 is adapted to be rotated and screwed into the myocardium during the introduction and fixation process as described above, or to extend from the lead 410 and screw into the myocardium 180 (FIG. 2) as extension occurs. Electrodes and fixation arrangements in accordance with the present invention may be combined with leads such as, for example, those disclosed in commonly assigned U.S. Pat. No. 5,496,362, which is hereby incorporated herein by reference. It is understood that fixation elements for cardiac leads in accordance with the present invention may also function as an electrode, or that the fixation elements may be independent of any electrodes. For example, a non-active helix may be used for fixation, and other electrodes may be provided in or on the lead 410.

An epicardial lead in accordance with the present invention may have, for example, the helical electrode 420 formed of fine platinum-iridium alloy wire having a diameter of about 0.006 inches that is drawn into a helix of a diameter between about 0.027 and about 0.058 inches. Dimensions other than those previously recited are also contemplated. The helical electrode 420 provides contact and attachment with the heart wall at a selected site appropriate for cardiac stimulation therapy.

The conductor 450 may be contained within an insulating sheath (not shown) of lead 410. The conductor 450 may be formed of an electrically insulated multi-strand cable or helical coil of materials typically used in pace/sense lead conductors, such as MP35N alloy having an overall diameter of about 0.003 to about 0.020 inches. Due to the small diameter, a more radio-opaque metal, e.g., platinum-iridium alloy helical coil or a silver core wire multi-strand cable, may be used to enhance visibility under fluoroscopy. The insulating sheath may be manufactured from silicone rubber or a dielectric fluoropolymer material, e.g., PTFE, ETFE or THV200, for example. In the latter case, the sheath may have a wall thickness of about 0.006 inches. The outer diameter of lead 410 is typically on the order of about 4 French for the unipolar epicardial pace/sense lead illustrated in FIG. 2, but is not limited to this diameter.

Referring now to FIGS. 4A through 4E, the lead 410 is shown in combination with a Doppler blood-flow sensor 470 in accordance with embodiments of the present invention. As described earlier, a suitable implantation site must be found before the helical electrode 420 is inserted into the myocardium 180 (FIG. 2). One method of determining a proper location is by use of the Doppler blood-flow sensor 470, to determine that no vessels are in the immediate vicinity of the sharp end 620 before inserting the helical electrode 420 into the myocardium 180. It is understood that the description of the Doppler blood-flow sensor 470 is only one non-limiting example of a sensor suitable for use in accordance with the present invention. The Doppler blood-flow sensor 470 may be replaced with any sensor configured to sense the presence of an anatomical feature or a physiological parameter in proximity with the lead body's distal end in accordance with the present invention. Other suitable sensors include, for example, tissue impedance sensors, perfusion sensors, photoplethysmograpic sensors, and blood oximetry sensors. For example, a perfusion sensor may be configured to differentiate between myocardial tissue including blood vessels and myocardial tissue without blood vessels using a colormetric measurement.

In the embodiment illustrated in FIGS. 4A through 4E, the sensor 470 is moveable within a lumen 411 of the lead 410. In the example of the helical electrode 420, the helix may be used solely for fixation, and may not be an electrode. The sensor 470 may also be extendable and retractable within the helix, as is illustrated by the relative positions of the sensor 470 between FIGS. 4A and 4D.

FIG. 4A illustrates the sensor guided epicardial lead 410 with the sensor 470 placed proximal to the distal end of a lead. The sensor 470, as is illustrated in FIG. 4A, may not require contact with the myocardium to sense a parameter. For example, the sensor 470 may be an optical fiber that transmits and receives light to provide sensing, thereby not requiring contact to make a measurement.

FIG. 4B illustrates the sensor guided epicardial lead 410 with the sensor 470 placed even with the end of the lead 410. This configuration may be particularly useful when the lead 410 utilizes an extendable/retractable configuration of the helical electrode 420 (as will be described more fully below with reference to FIG. 7). The configuration illustrated in FIG. 4B may provide for measurements from the sensor 470 before extension of the helical electrode 420

Figure 4C:
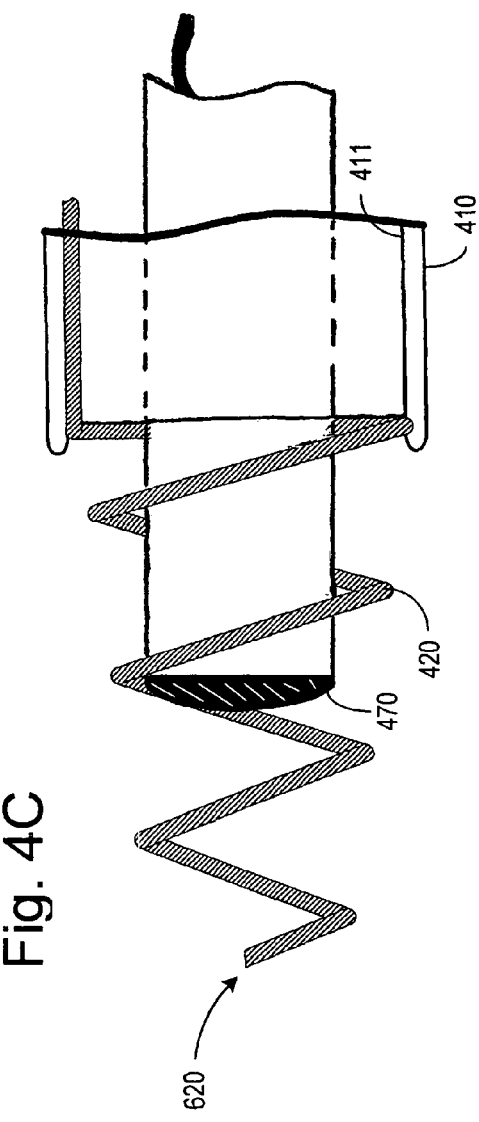
FIG. 4C illustrates a sensor guided epicardial lead in accordance with the present invention, with the sensor placed proximal to the distal end of a helical fixation element, and distal from the end of a lead.

FIG. 4C illustrates the sensor guided epicardial lead 410 with the sensor 470 placed proximal to the distal end of helical electrode 420, and distal from the end of the lead 410. The sensor 470, as is illustrated in FIG. 4C, may be particularly useful for fixed helical electrodes 420, combined with non-contact configurations of the sensor 470, such as optical versions described earlier.

Figure 4D:
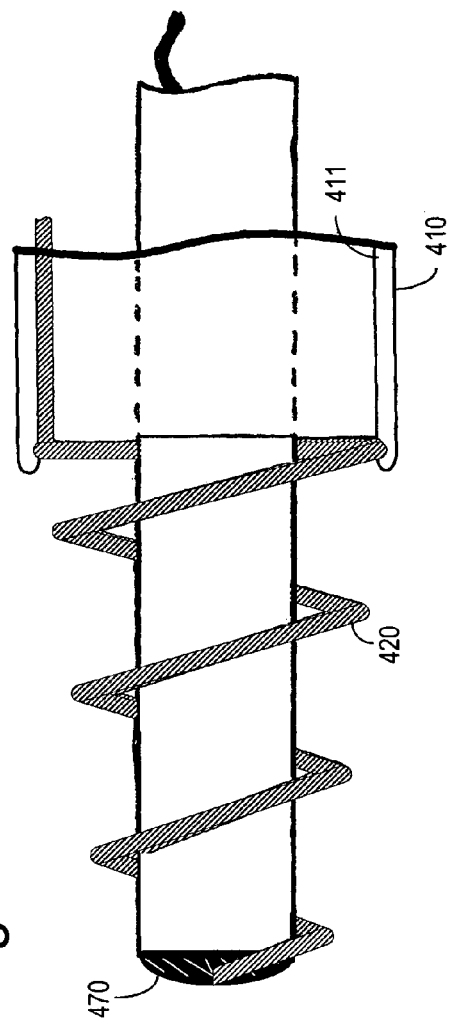
FIG. 4D illustrates a sensor guided epicardial lead in accordance with the present invention, with the sensor placed even with the distal end of a helical fixation element.

FIG. 4D illustrates the sensor guided epicardial lead 410 with the sensor 470 placed even with the distal end of helical electrode 420. This configuration may be particularly useful when the lead 410 utilizes a fixed configuration of the helical electrode 420. The sensor 470 may be used to sense a desired location for implantation.

Figure 4E:
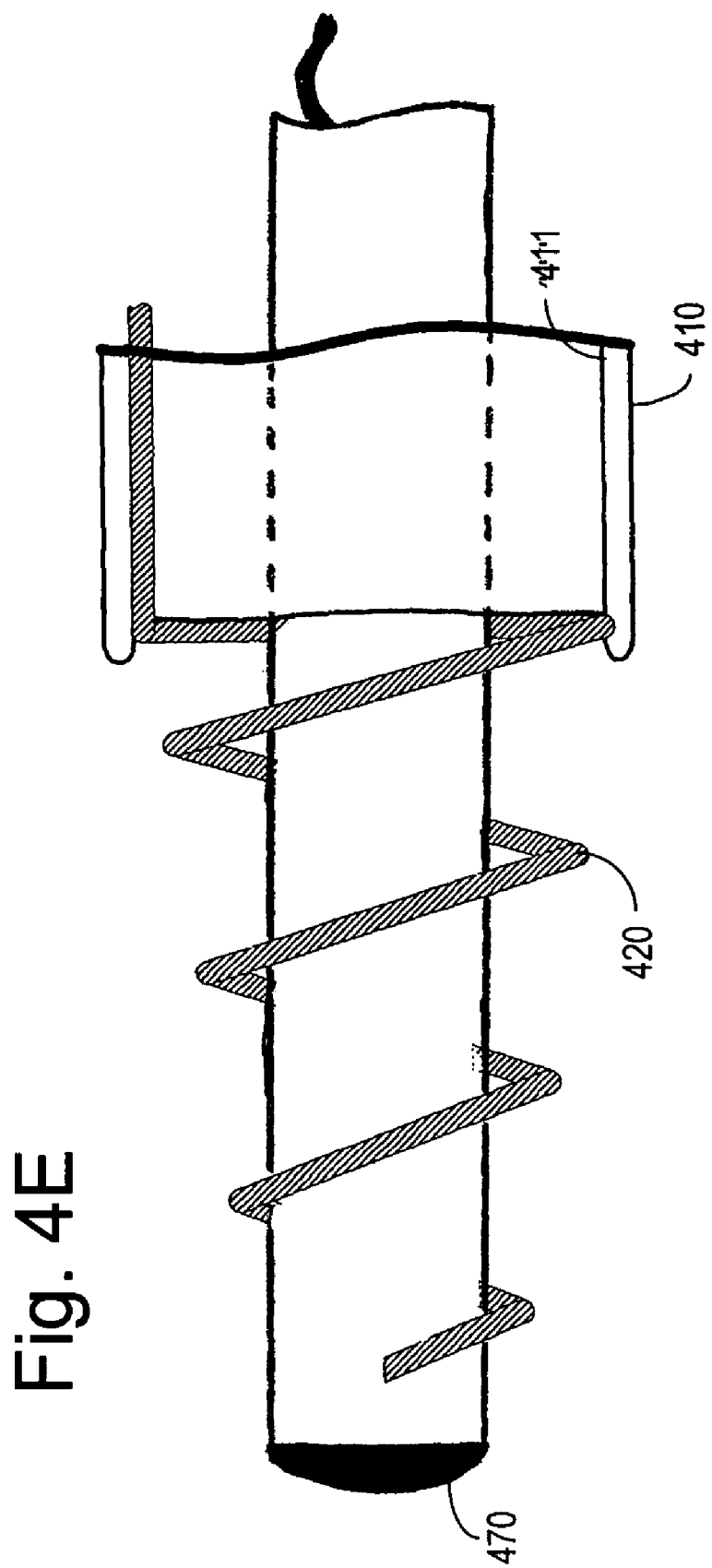
FIG. 4E illustrates a sensor guided epicardial lead in accordance with the present invention, with the sensor placed distal from the distal end of a helical fixation element.

FIG. 4E illustrates the sensor guided epicardial lead 410 with the sensor 470 placed distal from the distal end of helical electrode 420. This configuration may be particularly useful when the lead 410 utilizes a fixed configuration of the helical electrode 420. The sensor 470 may be used to sense a desired location for implantation, and subsequently guide the lead 410 to the implantation site. Extending the sensor 470 beyond the end of the lead 410, or out from another location of the lead 410, may further provide for intramyocardial placement of the sensor. In another embodiment, the sensor 470 may be incorporated into a tissue perforating tool or device that may be extended to perforate tissue at an implant site, and determine that no vessels are in the immediate vicinity before implanting the lead. In a further embodiment, the sensor 470 may function as illustrated in FIGS. 4A though 4E with the helix electrically inactive.

The Doppler blood-flow sensor 470 is illustrated separate from the lead 410 and alone in FIGS. 5A and 5B, and may be useful for blood-flow/perfusion sensing in the vicinity of a potential lead implant site in accordance with the present invention. The Doppler blood-flow sensor 470 may be a separate element of a lead system, insertable and removable within a lumen of the lead 410, or may be a rigid or movable component of a lead system, such as by attachment of the Doppler blood-flow sensor 470 at a distal end of the lead 410.

The Doppler blood-flow sensor 470 in FIGS. 5A and 5B uses an annular array 320, piezoelectric crystal arrangement. Any suitable arrangement, such as a phased array or fixed lens element system may be used without departing from the scope of the present invention. FIG. 5A is a magnified plan view of a distal end 310 of the Doppler blood-flow sensor 470. FIG. 5B is a magnified end view of the Doppler blood-flow sensor 470 illustrated in FIG. 5A. The annular array 320 includes a transmit ring 330 and a receive ring 340. As is shown in FIG. 5A, the Doppler blood-flow sensor 470 may also include a matching layer 350 and a lens 360 as is known in the art. Electrical conductors 370 connect the Doppler blood-flow sensor 470 to Doppler circuitry 375, such as stand-alone circuitry, circuitry provided with a pulse generator, or circuitry provided with an external programmer or other external system.

Figure 6:
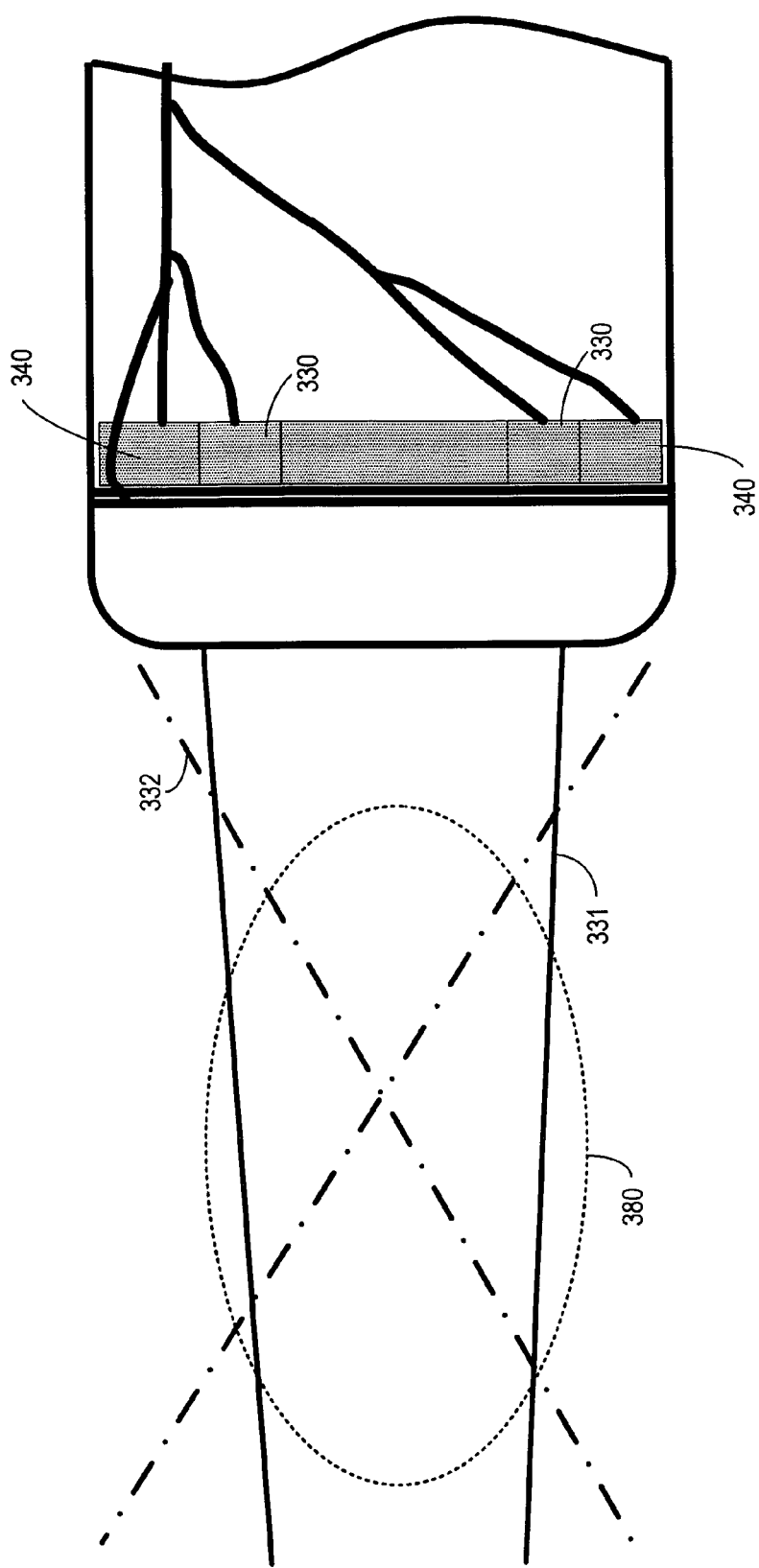
FIG. 6 is a magnified sectional view through the longitudinal axis of the lead illustrated in FIG. 5A, illustrating the ultrasonic beam pattern useful for detecting blood flow in the vicinity of a fixation element prior to implantation of an epicardial lead in accordance with an embodiment of the present invention.
Figure 7:
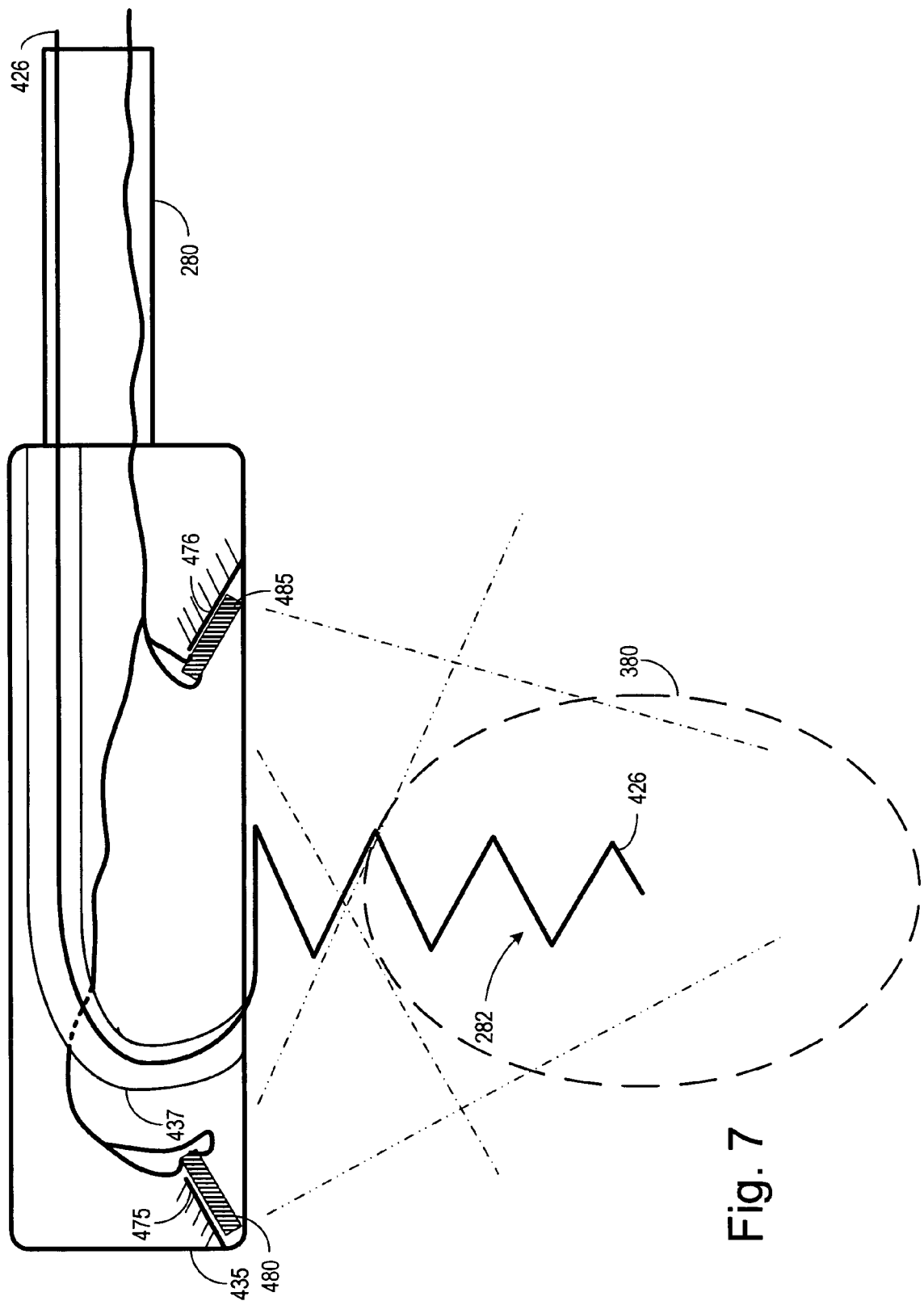
FIG. 7 is a magnified transparent plan view illustrating internal components of a lead having a fixation element positioned at 90 degrees relative to the lead's longitudinal axis, this view further illustrating an ultrasonic beam pattern useful for detecting blood flow in the vicinity of a fixation element prior to implantation of an epicardial lead in accordance with another embodiment of the present invention.

The Doppler circuitry 375 provides information about the presence of an anatomical feature or a physiological parameter of cardiac tissue in proximity with the lead body's distal end in accordance with the present invention. The annular array 320 is associated with the distal end 310 or fixation element end of the lead 410. As best shown in FIGS. 5 through 7, the Doppler blood-flow sensor 470 provides an ultrasonic energy directing arrangement using the lens 360 (Figures 5A and 6) and/or focused elements (FIG. 7) for directing the transmission and the reception of ultrasonic energy on the operational field 380.

In the embodiments of Doppler blood-flow sensor arrangements illustrated in FIGS. 5A through 7, the ultrasonic energy directing arrangements may include acoustic lenses. The acoustic lenses may be made from a number of materials well known in the art to focus the ultrasonic energy as described and shown. Accordingly, the acoustic lenses will not be further described herein.

Referring now to FIG. 6, ultrasonic energy is transmitted, using the transmit ring 330, to the operational field 380 of the lead 410 (FIGS. 4A through 4E) and reflected from the contents of the operational field 380. The ultrasonic energy reflected from the operational field 380 of the lead 410 is received, using the receive ring 340, and Doppler signals representative of the contents of the operational field are generated by the Doppler circuitry 375 (FIG. 5A) in response to the received ultrasonic energy. The Doppler signals are analyzed to determine the nature of the contents of the operational field of the lead 410 and the user of the lead 410 is informed of the contents of the operational field. If the contents of the operational field are confirmed as being appropriate for the lead implantation, the lead 410 may be implanted using a fixation element such as those described above.

A first beam pattern 331 is illustrated as an approximate plane wave, emanated from the transmit ring 330. A second beam pattern 332 is illustrated as a focused beam, focused in approximately the center of the operational field 380. As is known in the art, either ring 330, 332 may be useable as either a transmitting element or a receive element, or each element may be used in a pulsed mode as its own Doppler sensor. Providing at least one focused beam, such as the second beam pattern 332, allows the Doppler blood-flow sensor 470 to provide blood-flow information focused in the vicinity of the distal end of the lead 410. Providing both first beam pattern 331 and second beam pattern 332 beams focused energy to the area immediately in front of the Doppler blood-flow sensor 470, which may provide more detection specificity at the area of interest prior to implantation of a fixation element.

Referring to FIG. 7, the electrode 282 may be mounted to a lead 280 such as, for example, by mounting the electrode 282 to the distal end of the lead 280 such that electrode 282 extends perpendicularly to the longitudinal axis of the lead 280. The electrode may be fixed, or may be extendable and retractable, as illustrated in FIG. 7. Extendable/retractable electrodes useful in accordance with the present invention are described in commonly owned U.S. Pat. Nos. 6,270,496 and 6,574,514, which are hereby incorporated herein by reference.

In FIG. 7, the electrode 282 is pre-formed and biased to have a helical shape. The electrode 282 may be withdrawn into a head 435 when retracted. When properly positioned at the implant site, the electrode 282 may be extended through a guide or anvil 437, forming into the helical shape as the electrode 282 extends from the head 435, fixing it in place at the implant site.

In a Doppler blood-flow sensing arrangement 480, 485 illustrated in FIG. 7, the ultrasonic energy directing arrangement includes a mounting arrangement 475, 476 taking the form of mounting a first piezoelectric element 480 and a second piezoelectric element 485 secured to a head 435 of the lead 410. The head 435 supports the first piezoelectric element 480 and the second piezoelectric element 485, directing the ultrasound energy at the operational field 380.

The angular orientation of the pair of piezoelectric elements 480, 485 may be slightly different for each Doppler blood-flow sensing arrangement 480, 485 such that ultrasonic energy is directed to the operational field 380 occupied, for example, by a blood vessel. As stated previously, acoustic lenses may be used on one or both of the pair of the piezoelectric elements of the Doppler blood-flow sensing arrangement 480, 485 in place of, or in addition to, the angular orientation for directing ultrasonic energy associated with the Doppler blood-flow sensing arrangement 480, 485 toward or from the operating field 380. As is known in the art, two piezoelectric elements 480, 485 may be used, as illustrated in FIGS. 6 and 7, in continuous wave mode, and additionally or alternately, a single element may be used in a pulse-echo arrangement.

Whatever the form of the ultrasonic transducer, Doppler circuitry 375 (Illustrated in FIG. 5A) is provided for activating the transducer to transmit ultrasonic energy to the operational field defined by an associated lead, such as the lead 410 and/or the lead 48b. The Doppler circuitry 375 also provides for receiving signals generated by the transducer in response to received ultrasonic energy that is reflected from the operational field and for analyzing those signals. The Doppler circuitry 375 may be of a conventional circuit design as far as transmission and reception of ultrasonic energy and processing of the resulting signals is concerned.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of determining suitability for implanting a cardiac lead on a surface of a patient's heart, comprising:

accessing, via a patient's chest cavity, an epicardial surface of the heart;

moving the cardiac lead to an implant site at the epicardial surface;

stabilizing the lead at the implant site;

transmitting a signal from the lead directed at the implant site;

receiving at the lead a reflected signal resulting from the transmitted signal indicative of the presence or absence of a blood vessel at the implant site; and determining whether the implant site is suitable or unsuitable for implantation of the cardiac lead at least in part using the reflected signal.

2. The method of claim 1, comprising:

determining a physiological parameter at the implant site; and determining whether the implant site is suitable or unsuitable for implantation of the cardiac lead using the reflected signal and the physiological parameter.

3. The method of claim 1, further comprising generating blood-flow signals representative of blood vessel presence at or near the implant site using the reflected signal.

4. A method of determining suitability for implanting a cardiac lead on a surface of a patient's heart, comprising:

accessing, via a patient's chest cavity, an epicardial surface of the heart;

moving the cardiac lead to an implant site at the epicardial surface;

transmitting, from the cardiac lead, ultrasonic energy directed at the implant site;

receiving, at the cardiac lead, ultrasonic energy reflected from the implant site; and identifying the site as suitable or unsuitable for implanting the cardiac lead at least in part using the received ultrasonic energy.

5. The method of claim 4, further comprising detecting presence or absence of blood perfusion at the implant site using the received ultrasonic energy.

6. The method of claim 4, further comprising: detecting presence or absence of blood perfusion at the implant site using the received ultrasonic energy; and performing a pacing threshold test at the implant site;

wherein the site is identified as suitable for lead implantation in response to detecting an absence of blood perfusion at the site and obtaining an acceptable pacing threshold for the site.

7. A system for determining suitability for implanting a cardiac lead on a surface of a patient's heart, comprising:

means for accessing, via a patient's chest cavity, an epicardial surface of the heart;

means for moving the cardiac lead to an implant site at the epicardial surface;

means for transmitting a signal directed at the implant site;

means for receiving a reflected signal resulting from the transmitted signal indicative of blood perfusion at the implant site;

means for determining an electrical parameter of tissue at the implant site; and means for determining whether the implant site is suitable or unsuitable for implantation of the cardiac lead using the reflected signal and the electrical parameter.

8. A system for determining suitability for implanting a cardiac lead on a surface of a patient's heart, comprising:

means for accessing, via a patient's chest cavity, an epicardial surface of the heart;

means for moving the cardiac lead to an implant site at the epicardial surface;

means for transmitting ultrasonic energy directed at the implant site;

means for receiving ultrasonic energy reflected from the implant site; and means for identifying the site as suitable or unsuitable for implanting the cardiac lead at least in part using the received ultrasonic energy.

* * * * *